(12) United States Patent
Dinakaran et al.

(10) Patent No.: US 10,578,521 B1
(45) Date of Patent: Mar. 3, 2020

(54) SEALED AUTOMATIC FILTER SCANNING SYSTEM

(71) Applicant: American Air Filter Company, Inc., Louisville, NY (US)

(72) Inventors: Satish Dinakaran, Washington, NC (US); Kenneth Beacham, Washington, NC (US)

(73) Assignee: AMERICAN AIR FILTER COMPANY, INC., Louisville, KY (US)

( * ) Notice: Subject to any disclaimer, the term of this patent is extended or adjusted under 35 U.S.C. 154(b) by 83 days.

(21) Appl. No.: 15/591,881

(22) Filed: May 10, 2017

(51) Int. Cl.
 *G01N 1/22* (2006.01)
 *G01N 15/08* (2006.01)

(52) U.S. Cl.
 CPC ....... *G01N 1/2205* (2013.01); *G01N 15/0806* (2013.01); *G01N 2015/084* (2013.01)

(58) Field of Classification Search
 CPC .. G01N 2001/002; G01N 1/22; G01N 1/2205; G01N 1/2226; G01N 1/2247; G01N 2001/2285; G01N 15/084
 USPC .......................... 73/863, 863.23, 864, 864.31
 See application file for complete search history.

(56) References Cited

U.S. PATENT DOCUMENTS

| | | | |
|---|---|---|---|
| 2,898,485 A | 8/1959 | Richter et al. | |
| 3,765,225 A | 10/1973 | Rivers | |
| 4,184,090 A | 1/1980 | Taiani et al. | |
| 4,277,707 A | 7/1981 | Silver et al. | |
| 4,324,568 A | 4/1982 | Wilcox et al. | |
| 4,494,403 A | 1/1985 | Bowers et al. | |
| 4,641,065 A * | 2/1987 | Shibuki | H02K 41/035 310/13 |
| 4,850,779 A | 7/1989 | Cashell et al. | |
| 4,893,980 A | 1/1990 | Balter | |
| 4,901,578 A | 2/1990 | Brill, III | |

(Continued)

FOREIGN PATENT DOCUMENTS

| | | |
|---|---|---|
| CN | 103962361 A | 8/2014 |
| DE | 3027351 A1 | 2/1981 |

(Continued)

OTHER PUBLICATIONS

Zhang, et al. "A Blunt Sampling Probe Developed for an In Situ Leak Test of HEPA Filters in High-Level Laboratory". HVAC&R Research. vol. 20, Iss. 2, 2014.

(Continued)

*Primary Examiner* — Benjamin R Schmitt
(74) *Attorney, Agent, or Firm* — Middleton Reutlinger (57) ABSTRACT

The described embodiments relate to systems, methods, and apparatuses for collecting and testing particles emitted from a filter of a duct using an electromechanical scanning system that is contained within the duct. The electromechanical scanning system includes a stacked arrangement of ports that extend over a surface of the filter in order to collect particles that are passing through the filter. The stacked arrangement of ports is connected to a magnetic rail device that maneuvers the stacked arrangement of ports to, and between, distal ends of the filter. Control signals are sent to the magnetic rail device from a controller that is external to the housing and connected to electrodes located on a surface of the housing. The electrodes are sealed such that particles do not unintentionally escape from the duct.

21 Claims, 9 Drawing Sheets

(56) References Cited

U.S. PATENT DOCUMENTS

| | | |
|---|---|---|
| 5,105,932 A | 4/1992 | Bryson, III et al. |
| 5,224,585 A | 7/1993 | Blanco et al. |
| 5,388,086 A | 2/1995 | Yamasaki et al. |
| 5,415,483 A | 5/1995 | Franklin, Jr. |
| 5,514,925 A | 5/1996 | Worthington et al. |
| 5,955,798 A * | 9/1999 | Ishiyama ............ H02K 41/03 310/12.14 |
| 5,980,193 A | 11/1999 | Clifton et al. |
| 6,308,818 B1 | 10/2001 | Bonora |
| 6,679,671 B2 | 1/2004 | Blonigan et al. |
| 6,712,907 B1 | 3/2004 | Pratt et al. |
| 7,010,960 B1 | 3/2006 | Grantham |
| 7,028,831 B2 | 4/2006 | Veiner |
| 7,057,369 B2 | 6/2006 | Hoffmann |
| 7,439,735 B2 | 10/2008 | Bamabo et al. |
| 7,658,787 B2 | 2/2010 | Morse et al. |
| 7,758,664 B2 | 7/2010 | Morse et al. |
| 7,998,252 B2 | 8/2011 | Huza et al. |
| 8,408,046 B2 | 4/2013 | Xu et al. |
| 8,549,895 B2 | 10/2013 | Chung et al. |
| 9,062,694 B2 | 6/2015 | Fletcher et al. |
| 9,234,812 B2 | 1/2016 | Krywyj |
| 9,360,411 B2 | 6/2016 | Woolard et al. |
| 9,821,911 B2 | 11/2017 | Wallbott et al. |
| 2006/0151013 A1 | 7/2006 | Tsuneta et al. |
| 2006/0272301 A1* | 12/2006 | Morse ............ B01D 46/0086 55/439 |
| 2011/0266904 A1 | 11/2011 | Stefanini et al. |
| 2012/0024694 A1 | 2/2012 | Mullapudi et al. |
| 2016/0096135 A1 | 4/2016 | Woolard |
| 2016/0097705 A1 | 4/2016 | Woolard |

FOREIGN PATENT DOCUMENTS

| | | |
|---|---|---|
| EP | 1057515 A1 | 12/2000 |
| EP | 2196250 B1 | 2/2012 |
| EP | 2090350 B1 | 5/2013 |
| JP | 2929390 B2 | 8/1999 |
| JP | 4423627 B2 | 3/2010 |
| TW | 201223616 A | 6/2012 |

OTHER PUBLICATIONS

Technical Datasheet, Unguided Linear Motion, MPP Series, UHV Design Ltd., Jurt J.Lesker Company, Retrieved on Dec. 4, 2017 from www.lesker.com.

* cited by examiner

SEALED AUTOMATIC FILTER SCANNING SYSTEM

TECHNICAL FIELD

The present invention is directed generally to air filter testing. More particularly, various systems, methods, and apparatuses disclosed herein relate to testing an air filter using a linear drive motor that is contained within an air duct with the air filter.

BACKGROUND

Air filters can be crucial to the operation of many ventilation systems that rely on filters to remove certain particles from the air. For this reason, certain air filters often undergo tests wherein particles emitted from or passing through the air filters are scanned. Such tests can be volatile because air ducts can often include apertures that allow external particles to penetrate the air ducts. Furthermore, some testing methods employ mechanical parts that can excrete particles as a result of friction between the mechanical parts. Such rogue particles can impede sensor measurements, resulting in inaccurate tests that must be repeated until correct results are provided.

SUMMARY

The present disclosure is directed to systems, methods, and apparatuses for automatically testing a filter using a particle sampling system sealed within, or external to, a duct. In some embodiments, a system is set forth as having a duct comprising an air input portion and an air output portion. The system can also include a fitter receptacle disposed within the duct and configured to receive a filter between the air input portion and the air output portion. The system can further include a particle sampling system configured to collect samples of particles moving through the filter. The particle sampling system can include a coil that is connected to a stacked arrangement of ports and a magnetic rail. The coil can be configured to traverse the magnetic rail and navigate the stacked arrangement of ports across the filter as particles are moving through the filter.

In other embodiments, a method is set forth for operating a particle sampling system that includes a coil for maneuvering a column of sampling ports along a magnetic rail. The method can include steps of causing gas to move through an intake portion of a duct that contains the particle sampling system and a filter that filters the gas, and receiving, at the coil, a control signal from a controller that is external to the duct. The controller can cause the coil to traverse the magnetic rail. The method can further include a step of moving the column of sampling ports along a length of the filter. The column of sampling ports can be attached to the coil and move in response to the coil receiving the control signal. The method can also include a step of causing filtered gas to move through sampling ports of the column of sampling ports and out of the duct to an external particle sensor.

In yet other embodiments, a particle sampling system is set forth. The particle sampling system can include an array of ports configured to receive filtered particles passing through a filter that is mounted within an air duct. The particle sampling system can also include a linear drive that includes a magnetic rail and a coil. The linear drive can be connected to the array of ports and configured to maneuver the array of ports over a surface of the filter. The particle sampling system can further include a support plate connected to the array of ports and the linear drive. The support plate can be configured to transfer mechanical energy from the coil to the array of ports and maintain a position of the array of ports between the filter and the linear drive.

The term "controller" is used herein generally to describe various apparatus relating to the operation of one or more devices. A controller can be implemented in numerous ways (e.g., such as with dedicated hardware) to perform various functions discussed herein. A "processor" is one example of a controller, which employs one or more microprocessors that may be programmed using software (e.g., machine code) to perform various functions discussed herein. A controller may be implemented with or without employing a processor, and also may be implemented as a combination of dedicated hardware to perform some functions and a processor (e.g., one or more programmed microprocessors and associated circuitry) to perform other functions. Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media (generically referred to herein as "memory," e.g., volatile and non-volatile computer memory such as RAM, PROM, EPROM, and EEPROM, floppy disks, compact disks, optical disks, magnetic tape, etc.). In some implementations, the storage media may be encoded with one or more programs that, when executed on one or more processors and/or controllers, perform at least some of the functions discussed herein. Various storage media may be fixed within a processor or controller or may be transportable, such that the one or more programs stored thereon can be loaded into a processor or controller so as to implement various aspects of the present invention discussed herein. The terms "program" or "computer program" are used herein in a generic sense to refer to any type of computer code (e.g., software or machine code) that can be employed to program one or more processors or controllers.

In one network implementation, one or more devices coupled to a network may serve as a controller for one or more other devices coupled to the network (e.g., in a master/slave relationship). In another implementation, a networked environment may include one or more dedicated controllers that are configured to control one or more of the devices coupled to the network. Generally, multiple devices coupled to the network each may have access to data that is present on the communications medium or media; however, a given device may be "addressable" in that it is configured to selectively exchange data with (i.e., receive data from and/or transmit data to) the network, based, for example, on one or more particular identifiers (e.g., "addresses") assigned to it.

The term "network" as used herein refers to any interconnection of two or more devices (including controllers or processors) that facilitates the transport of information (e.g., for device control, data storage, data exchange, etc.) between any two or more devices and/or among multiple devices coupled to the network. As should be readily appreciated, various implementations of networks suitable for interconnecting multiple devices may include any of a variety of network topologies and employ any of a variety of communication protocols. Additionally, in various networks according to the present disclosure, any one connection between two devices may represent a dedicated connection between the two systems, or alternatively a non-dedicated connection. In addition to carrying information intended for the two devices, such a non-dedicated connection may carry information not necessarily intended for either of the two devices (e.g., an open network connection). Furthermore, it should be readily appreciated that various networks of devices as discussed herein may employ one or more wireless, wire/cable, and/or fiber optic links to facilitate information transport throughout the network.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION

The described embodiments relate to systems, methods, and apparatuses for collecting and testing particles emitted from or collected by a filter of a duct using an electromechanical scanning system that is contained within the duct. Filter testing can be essential for ensuring that a filter is adequately preventing certain particles from passing through an air duct. However, results of such testing can be rendered inaccurate as a result of insufficient sealing of testing systems, and the generation of rogue particles from moving parts within the testing system. For example, certain testing systems can rely on external driving mechanism that transfers motion through the duct wall to an internal mechanical motion system. This can cause wear and tear of couplings and fittings at the duct wall, and potentially create a breach in the envelope. Also, the moving mechanisms inside the wall themselves can generate particles due to friction. In order to overcome such deficiencies, the embodiments set forth herein rely on both a driving mechanism and an electromechanical motion system to be contained inside the duct with only the electronic signal to communicate with the driving mechanism coming from outside. Also, the electromechanical motion system can operate such that there is minimal friction occurring during operation. The electromechanical motion system can be controlled by a controller that is external to the duct and transmits electrical signals via one or more electrodes located at one or more surfaces of the duct.

In some embodiments, a particle sampling system is set forth herein as including a linear drive motor and an arrangement of ports connected to the linear drive motor. The linear drive motor can include a magnetic rail that includes a series of abutting magnets with one or more coils wound around or adjacent to the magnetic rail, leaving a gap between the coils and the magnets. Each coil can receive a control signal from the controller for maneuvering the coil over the magnetic rail and guiding the arrangement of ports along a surface of a filter for testing. The control signals provided to the coils can be separate phases for attracting and repelling the various magnets in the magnetic rail. In some embodiments, the magnetic rail can be an electromagnet capable of having a variable magnetic field. By having a coil that is separated from the magnetic rail by a gap, friction between moving parts can be eliminated, thereby reducing the prevalence of rogue particles within the duct during testing.

The duct can include one or more electrodes and one or more gas outlets for interacting with the particle sampling system from the outside of the duct. The electrodes can be located on a surface of the duct and can provide a conductive pathway between an external contact of the electrode and an internal contact of the electrode. The internal contact can be connected to the linear drive motor and/or any other electronic device of the particle sampling system, and the external contact can be connected to a controller and/or power supply for powering and controlling the particle sampling system. A gas outlet can be provided at a surface of the duct for transferring particles that have been emitted from the filter to one or more sensors that are external to the duct. The filtered particles can be captured by one or more of the ports that are connected to the coil. The ports can be in a stacked or column arrangement such that each port faces a different portion of the filter. Each port can be connected to a tube or channel that directs the filtered particles from a port to the gas outlet, and thereafter to the sensor. In some embodiments, the sensor can be a particle counter that is located outside the duct and pulls air samples from the port through the gas outlet. The sensor can provide data to the controller or other computing device that is tasked with interpreting sensor data related to the particles emitted from the filter. By locating the sensors external to the duct, there can be less operational parts within the duct, and thus less chance of rogue particles interfering with the testing process.

Figure 1:
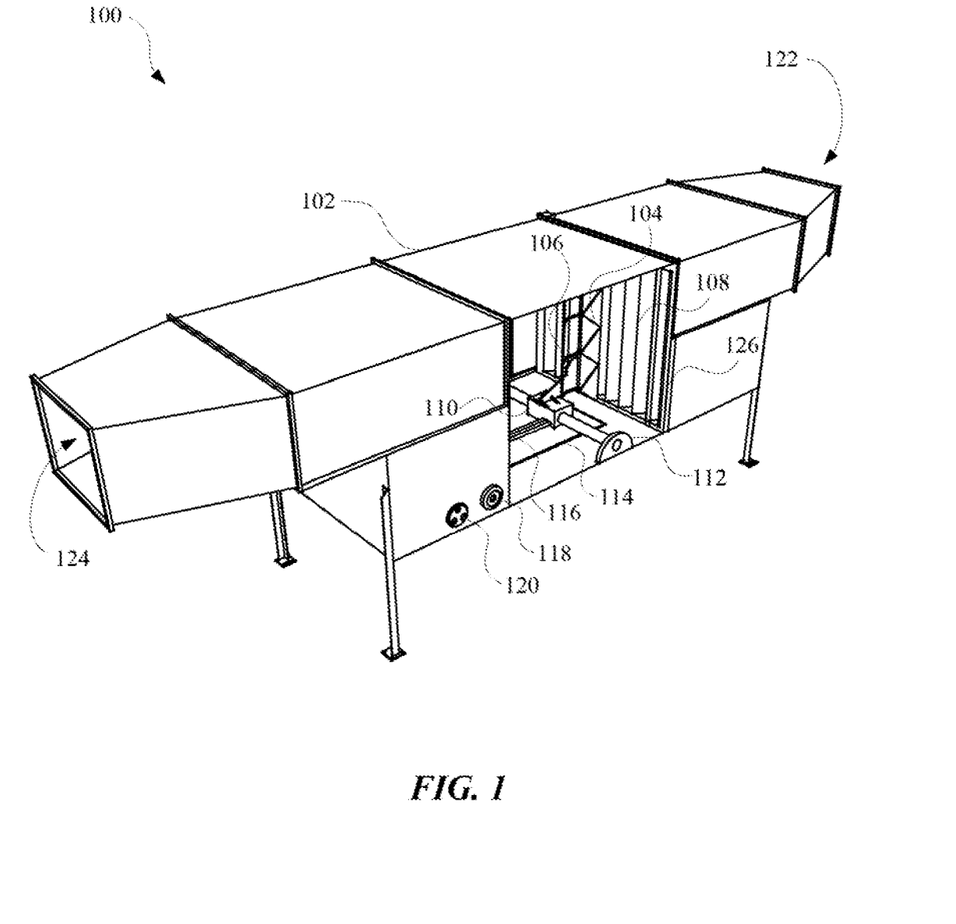
FIG. 1 illustrates a perspective view of a duct that includes a particle sampling system sealed within the duct.

FIG. 1 illustrates a perspective view 100 of a duct 102 that includes a particle sampling system sealed within the duct 102. The duct 102 can include an input portion 122 and an output portion 124 for receiving and emitting gas, respectively. The gas that flows through the duct 102 can be air, vapor, or any other process gas that can be passed through a duct 102. The duct 102 can include a filter 108 that is disposed within a filter receptacle 126 for keeping the filter 108 in place while gas is passing through the duct 102. The filter 108 can include layers of material that are structured to allow certain particles in the gas to pass through the duct 102, and prevent other particles from leaving the output portion 124. In order to ensure that the filter 108 is properly filtering the particles that are intended to be suspended by the filter 108, a particle sampling system can be sealed within the duct 102 for collecting and testing particles emitted by the filter 108.

The particle sampling system can include an arrangement of ports 104 that face the filter 108 in order that particles emitted from the filter 108 will pass into the ports 104. The ports 104 can be arranged in a stack or column that extends parallel to a surface of the filter 108, as illustrated in FIG. 1. Each port 104 can be connected to a channel 106 that allows gas that enters the ports 104 to move from the ports 104 out of the duct 102. For example, each channel 106 can be connected to a branch valve that consolidates the gases from the ports 104 into a single gas sample line 114. The gas sample line 114 can be connected to a gas output port 118, which can be connected to an external sensor that can provide data related to properties of the particles collected by the ports 104. The external sensor can be connected to a controller that can also control the movement of the particle sampling system by way of control signals that are transmitted to a linear drive system 110.

The linear drive system 110 can be attached to the ports 104 in order to move the ports 104 across the face of the filter 108. The linear drive system 110 can include a magnetic rail and one or more coils that can traverse the magnetic rail in response to receiving a control signal. For example, the magnetic rail can include a series of magnets, and each magnet can be attracted and/or repelled by one or more coils of the linear drive system 110. An air gap can be between the coil and the magnetic rail in order to eliminate any friction between coil and the magnetic rail, thereby reducing the amount of rogue particles in the duct 102. The gap can be between 0.5 millimeters and 5 millimeters. Alternatively, the gap can be less than 0.5 millimeters or greater than 5 millimeters. Rogue particles can be particles that originate from moving parts that emit the particles in response to friction, or external particles that enter the duct 102 through openings or inadequate seals, apart from the input portion 122 and output portion 124. The linear drive system 110 can be attached to a rail support 112 that can maintain a position of the linear drive system 110. A width of the rail support 112 can be equal to or less than a width of a side or edge of the filter receptacle 126. As the coil of the linear drive system 110 moves, the coil can cause the ports 104 to move with the coil in order that the ports 104 can collect particles from different locations on the filter 108. Control signals provided to the linear drive system 110 can be provided through one or more cables 116 that can be attached to the linear drive system 110 and one or more electrodes 120 connected to a surface of the duct 102. The electrodes 120 can provide a conductive pathway from the outside to the inside of the duct 102, without allowing particles external to the duct 102 from entering the duct. The electrodes 120 can be used to connect power to the linear drive system 110 and/or control signals to the linear drive system 110. Furthermore, the electrodes 120 can include separate phase connections for providing different control signals to different coils of the linear drive system 110. The cables 116 and gas sample line 114 can be flexible, in order that they can move out of the way of the motions of the linear drive system 110. The linear drive system 110 can programmatically oscillate between distal ends of the filter 108 simultaneous to gas flowing from the input portion 122 to the output portion 124. By providing a single arrangement of ports 104 that can move across the entire filter 108, less gas will be impeded by including too many objects within the duct 102.

Although the linear drive system 110 is illustrated in FIG. 1 as being a one dimensional drive, it should be noted that the linear drive system 110 can be arranged to move in two dimensions or three dimensions. In some embodiments, multiple linear drive systems 100 can be included in the duct 102, and the multiple linear drive systems 110 can maneuver one or more ports 104 in two or three dimensions over a surface of the filter 108. In some embodiments, the linear drive system 110 can move in response to feedback generated at a controller that controls the linear drive system 110. For example, the linear drive system 110 can position the ports 104 based on sensor data that relates to the particles collected by the ports 104. The controller can control the linear drive system 110 according to the parameters established for a testing operation, which can limit the testing according to time and/or volume of particles collected from the ports 104.

Figure 2:
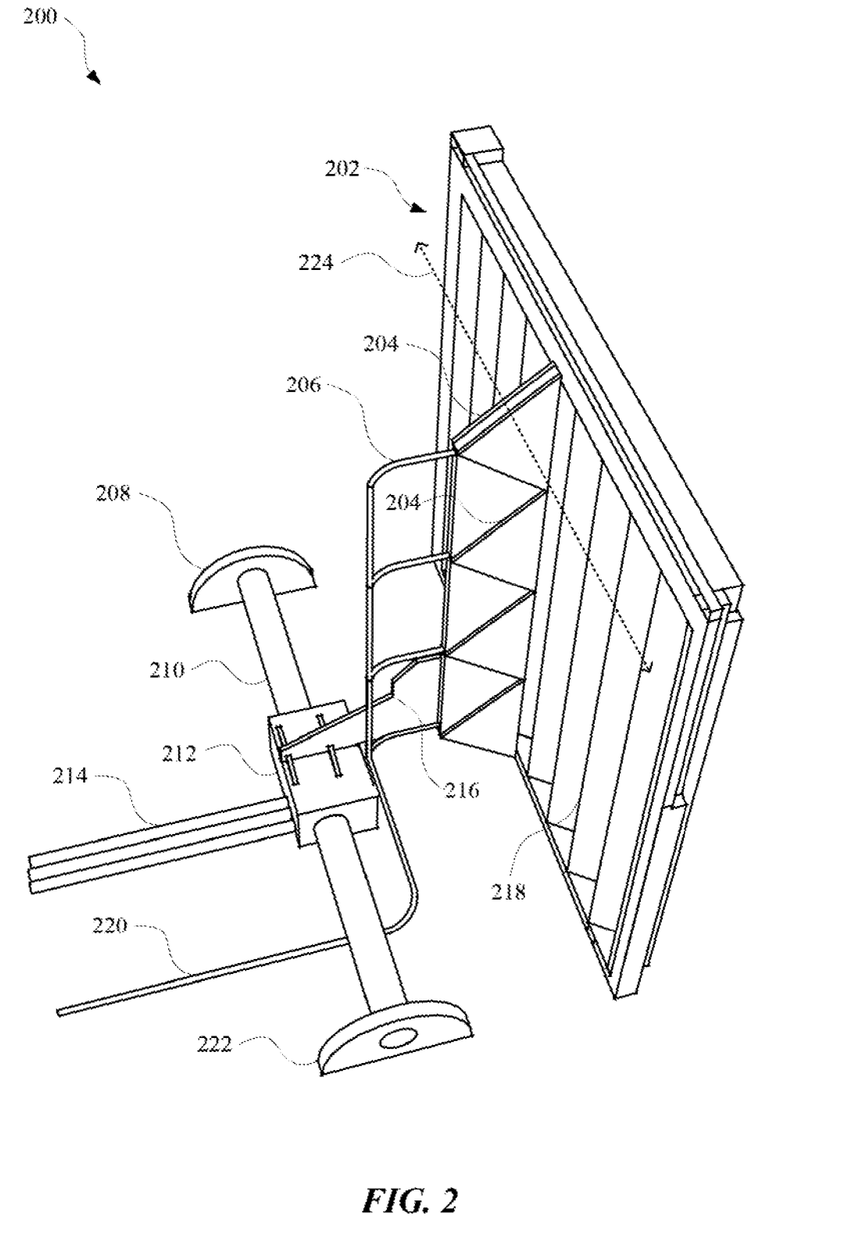
FIG. 2 illustrates a detailed view of a particle sampling system adjacent to a filter.

FIG. 2 illustrates a detailed view 200 of a particle sampling system adjacent to a filter 202. The particle sampling system can include an arrangement of ports 204 that can extend in a substantially parallel direction relative to the filter 202. The particle sampling system and filter 202 can be sealed within a duct for testing the filter 202. The ports 204 can be openings that allow filtered particles to enter while the ports 204 are moving across a width 224 of the filter 202. The ports 204 can move according to the motion of a drive component 212 that traverses a rail 210 in response to the drive component 212 receiving, via cables 214, a control signal from a controller that is external to the duct. The drive component 212 can include a housing that at least partially envelops one or more coils that can provide varying electromagnetic fields in response to receiving the control signals. The housing can include apertures through which the rail 210 can extend and connect to a first rail support 208 and a second rail support 222. Each of the first rail support 208 and the second rail support 222 can include apertures for containing the ends of the rail 210. The width of the rail 210 can be less than, equal to, or greater than a width of the filter 202. The rail 210 can be attached to the arrangement of ports 204 by a bracket 216 that can be secured to a surface of the drive component 212 and a surface of the arrangement of ports 204. The bracket 216 can be made from a rigid material and be attached to the arrangement of ports 204 at multiple points on the arrangement of ports 204 in order to ensure that the arrangement of ports 204 does not tilt or bend. Multiple channels 206 can extend from the arrangement of ports 204 in order to carry gas collected by the ports 204 to a test sample line 220 that can dispel the gas from the duct to a sensor. The sensor can then provide data related to the gas collected by the particle sampling system. The channels 206 can be connected to the test sample line 220 by a branch valve, which can be a connector that consolidates fluid from multiple sources into a single output from the connector.

The rail 210 can be a magnetic rail that includes multiple permanent magnets and/or multiple electromagnets powered by a source external to the duct in which the rail is disposed. The permanent magnets can be in a serial arrangement and surrounded by a housing that can include a curved surface that can provide an aerodynamic pathway for the gas moving through the duct. The coils of the drive component 212 can be separated from the housing of the magnets by a gap that eliminates friction as the drive component 212 moves between the first rail support 208 and the second rail support 222. In some embodiments, the rail 210 can include a flat surface that can be magnetically repelled and/or attracted by the coils in the drive component 212. By including a flat surface, the electromagnetic force of the coils acting on the flat surface will ensure that the arrangement of ports 204 remains upright and substantially parallel to a surface 218 of the filter 202. In some embodiments, the flat surface of the rail 210 can be parallel to a surface of the duct and normal to a direction in which the arrangement of ports 204 extends. Furthermore, the arrangement of ports 204 can extend below the flat surface of the rail 210. In some embodiments, an end of the arrangement of ports 204 most proximate to the drive component 212 can extend between the drive component 212 and the filter 202. In other words, an end of the arrangement of ports 204 can be adjacent to both the drive component 212 and the surface 218 of the filter 202. This configuration can ensure that a pathway from the filter 202 through the rest of the duct will not be obstructed by the drive component 212. Furthermore, positioning the drive component 212 and rail 210 adjacent to a lower edge of the filter 202 can ensure that minimal resistance is experienced by the gases moving through the vent, potentially interfering with filter testing processes.

Figure 3:
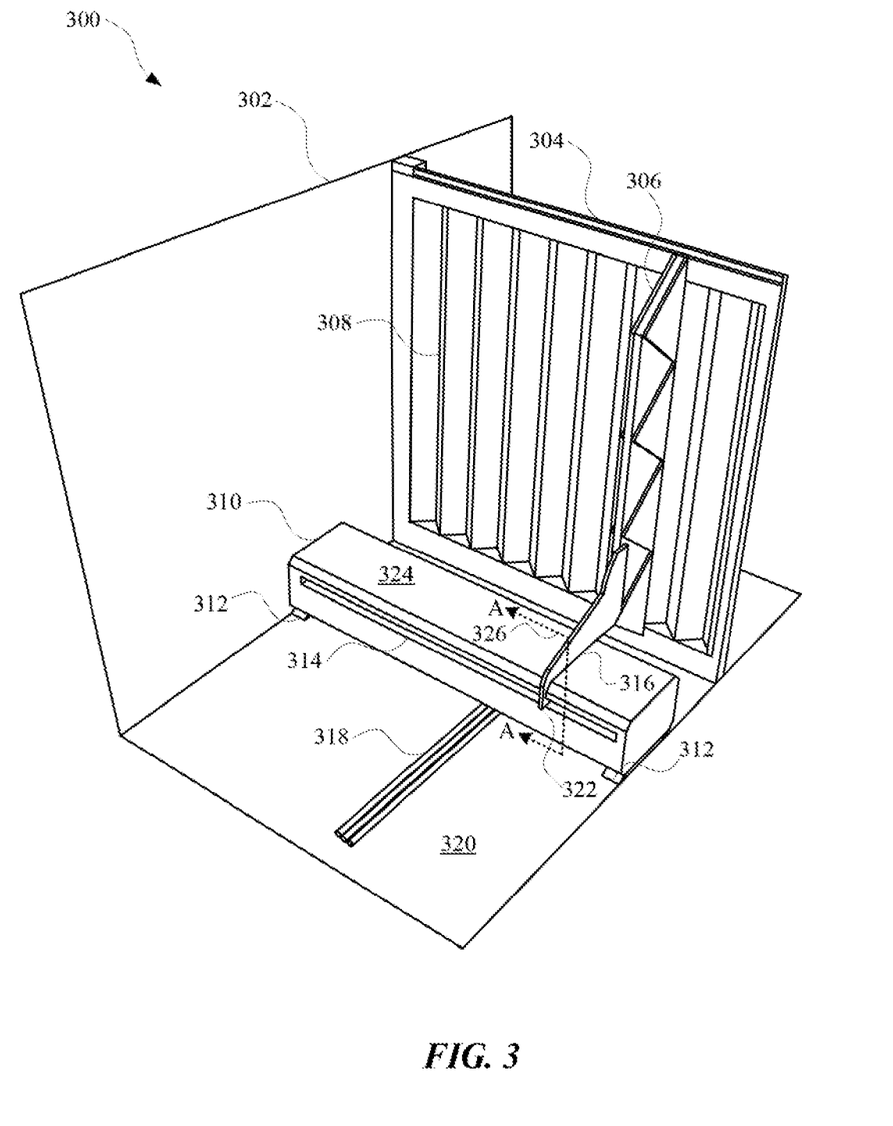
FIG. 3 illustrates a cut-away view of a duct containing a particle sampling system that includes a covered linear drive system.

FIG. 3 illustrates a cut-away view 300 of a duct 302 containing a particle sampling system that includes a covered linear drive system 310. The covered linear drive system 310 can be used to maneuver a column of ports 306 along a surface of a filter 308, which can be held in place by a filter receptacle 304 of the duct 302. The column of ports 306 can be maneuvered during a testing process of the filter 308 using control signals that are transmitted through cables 318 to the covered linear drive system 310. The control signals can be received by one or more coils that are inside of the covered linear drive system 310. The coils can be caused to repel and/or attract magnets inside the covered linear drive system 310. A housing 324 of the covered linear drive system 310 can include an opening 314 that extends across a majority of a length of the housing 324, or at least half of the housing 324 of the linear drive system 110. The opening 314 can allow for a bracket 316 to extend into the opening 314 and connect to the coils or other moving portion of the covered linear drive system 310. The bracket 316 can include a hook portion 322 that extends over a top surface of the housing 324, down a side of the housing 324 that faces away from the ports 306, and into the opening 314. By arranging the opening 314 in this way, any particles emitted from the filter 308 will not enter the opening 314 and risk damaging the moving parts within the covered linear drive system 310.

The covered linear drive system 310 can include multiple supports 312 that displace the housing 324 of the covered linear drive system 310 from an inner surface 320 of the duct 302. By displacing the housing 324 in this way, any vibrations occurring at the covered linear drive system 310 will not induce friction between a bottom surface of the housing and the inner surface 320 of the duct 302. In some embodiments, an end of the column of ports 306 can terminate between a top surface of the housing 324 of the covered linear drive system 310 and the inner surface 320. In this way, any ports 306 located between the top surface of the housing 324 and the inner surface 320 are free to be maneuvered by the covered linear drive system 310 between, and to, distal ends of the filter 308. The control signals supplied to the covered linear drive system 310 can cause the ports 306 to oscillate between the distal ends of the filter 308, simultaneous to gas passing through the duct 302. Particles collected by the ports 306 can be passed to an external sensor that can be connected to a computer device, which can determine a quality of the filter 308. Furthermore, an operation of the covered linear drive system 310 can change according to one or more features of the filter 308, as identified by the computing device. For example, the computing device can cause the covered linear drive system 310 to collect particles at certain areas of the filter 308 that have been identified by the computing device a volatile, such as the edges near the filter receptacle 304 that surrounds the filter 308.

Figure 4:
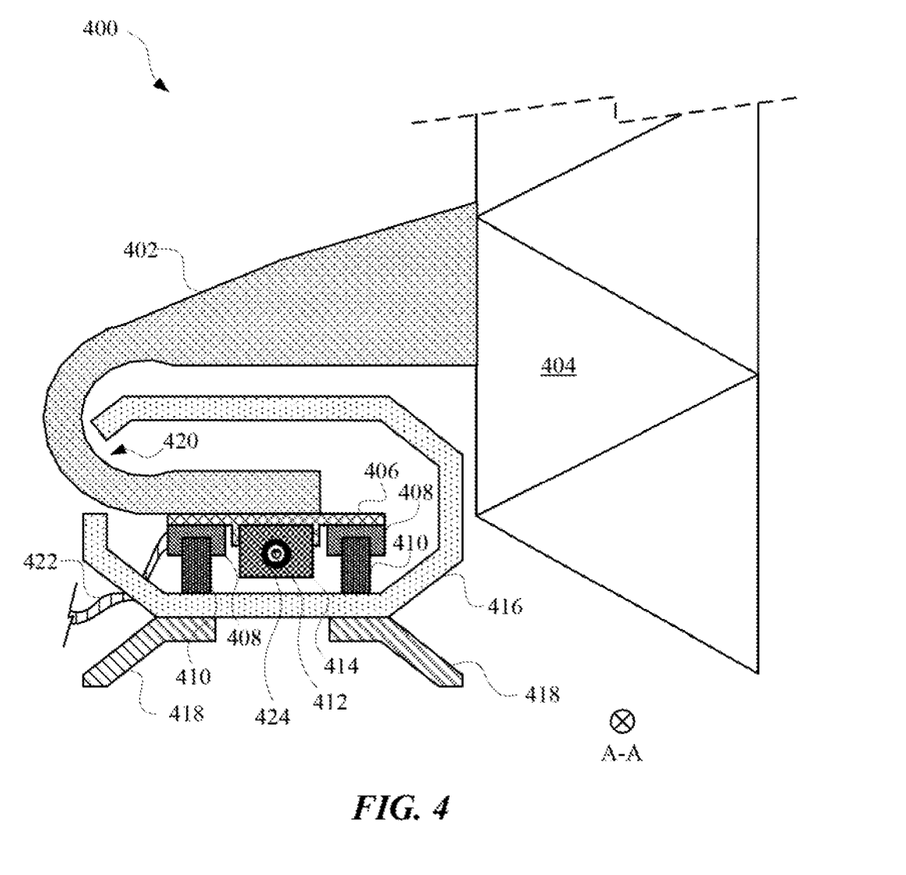
FIG. 4 illustrates a cross-sectional view of a cross-section (A-A) of the covered linear drive system provided in FIG. 4.

FIG. 4 illustrates a cross-sectional view 400 of a cross-section 326 (A-A) of the covered linear drive system 310 provided in FIG. 3. Specifically, the cross-sectional view 400 provides details of the covered linear drive system 310 according to some embodiments. The covered linear drive system 310 can include a housing 416 that at least partially envelops the moving parts of the covered linear drive system 310. The housing 416 can include an opening 420 in which a curved bracket 402 can extend out of. The curved bracket 402 can be attached to a column of ports 404 and a plate 406. The column of ports 404 can be used to test a filter that filters gas passing through a duct, and the covered linear drive system and be contained within the duct. It should be noted that only a partial view of the column of ports 404 is illustrated in FIG. 4.

The plate 406 can be directly or indirectly attached to the curved bracket 402 and maneuver the curved bracket 402 according to control signals that are transmitted to the covered linear drive system from a controller via cables 422. The cables 422 can include one or more conductive pathways for transmitting control signals and/or power to the covered linear drive system. The cables 422 can enter the housing 416 and provide control signals to a driver 414 of the covered linear drive system. The cables 422 can be embodied in a chain or receptacle that can move with the driver 414 while the driver 414 is moving along the rail 412. In this way, the cables 422 will not create any excess drag on the driver 414.

The driver 414 can include one or more coils 424 surrounded by a rigid housing with an aperture through which a rail 412 can be positioned. The rail 412 can include one or more magnets or electromagnets that provide a magnetic field that can interact with a magnetic field created by the coils 424 of the driver 414. When the coils 424 of the driver 414 receive the control signals, the coils 424 can generate the magnetic field that interacts with the magnetic field of the rail 412 for effectuating mechanical motion of the plate 406. A gap can exist between the rail 412 and an aperture of the driver 414 in order to eliminate friction that would otherwise occur during motion of the curved bracket 402. The plate 406 can be attached to the driver 414 and one or more guide mounts 408 that can extend over one or more guides 410. The guide mounts 408 and guides 410 can operate to direct a motion of the plate 406 during operation of the covered linear drive system. In some embodiments, the guide mounts 408 and guides 410 can be separated by a gap that is created by a magnetic repulsion of magnets in the guide mounts 408 and the guides 410. By including a gap between the guide mounts 408 and the guides 410, friction can be eliminated during operations of the covered linear drive system. Furthermore, friction can be further eliminated by incorporating legs 418 at a bottom surface of the housing 416 in order to offset the bottom surface of the housing 416 from a surface of a duct.

Figure 5:
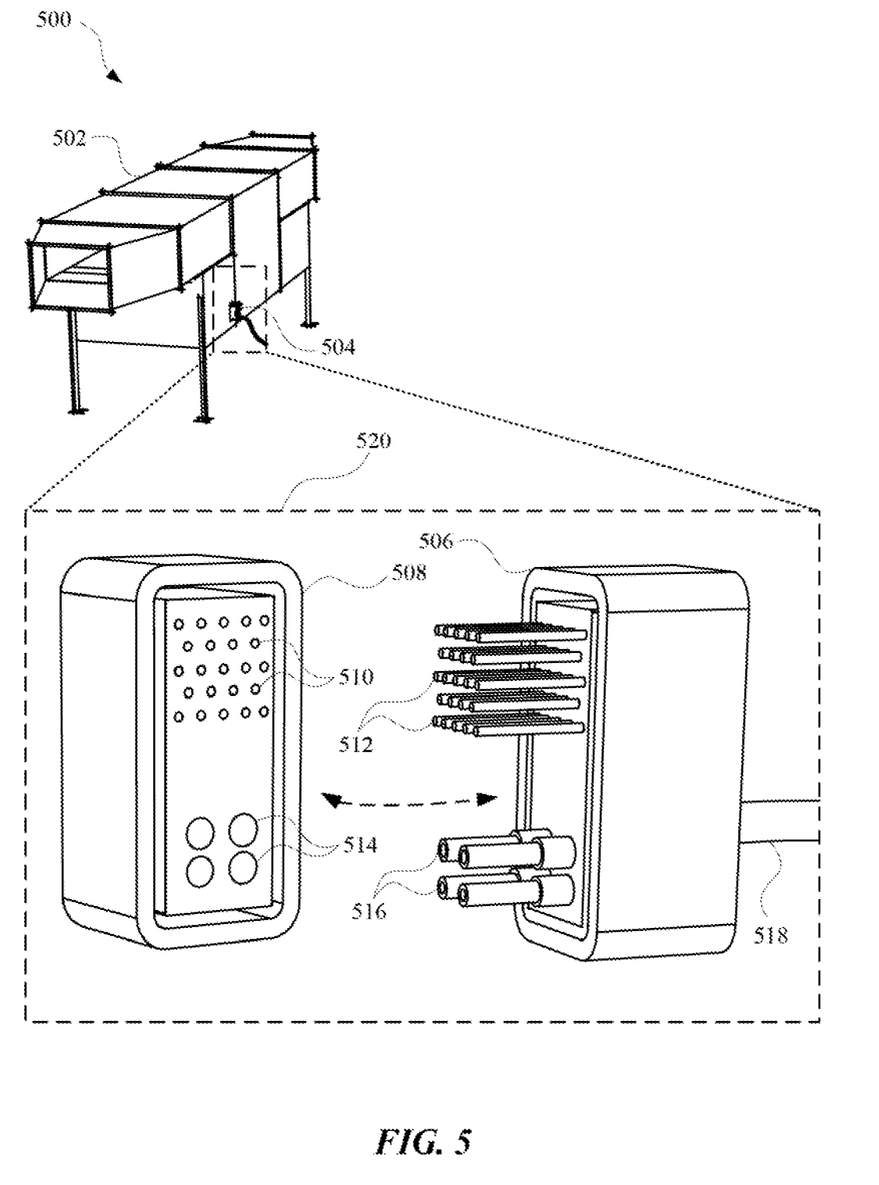
FIG. 5 illustrates a perspective view of a duct that can include a particle sampling system and a single connector for providing a gas outlet and electrodes for the particle sampling system.

FIG. 5 illustrates a perspective view 500 of a duct 502 that can include a particle sampling system and a single connector 504 for providing a gas outlet and electrodes for the particle sampling system. The connector 504 is illustrated in further detail in view 520, where a receptacle 508 and an adapter 506 are shown as parts of the connector 504. The receptacle 508 can be a portion of the connector 504 that is mounted to a surface of the duct 502. The receptacle 508 can include electrodes 510 for transmitting control signals and/or power signals to the particle sampling system of the duct 502. The receptacle 508 can further include sampling outlets 514 for providing sample particles to sensors that are external to the duct 502 via a cable 518. The sampling outlets 514 and electrodes 510 can receive adapter electrodes 512 and adapter sampling inlets 516, respectively, when the receptacle 508 is connected to the adapter 506. The adapter electrodes 512 of the adapter 506 can be conductive pins that extend from the adapter 506 for providing control signals and/or power to the particle sampling system. The adapter sampling inlets 516 can receive particles collected by the particle sampling system and transmitted through the sampling outlets 514. Both the adapter sampling inlets 516 and adapter electrodes 512 can be connected to the cable 518, which can include one or more wires for transmitting control signals and/or power, and one or more tubes for transmitting particles. In this way, the particle sampling system can be sealed within the duct 502 in such a way that only a single connector 504, or alternatively multiple connectors in some embodiments, for controlling the particle sampling system during a filter testing process. This reduces the risk of external particles penetrating the duct 502 and affecting the filter testing process. In some embodiments, the receptacle 508 and the adapter 506 connect using a mechanical connection such as a snap and lock device, or a magnetic connection where a magnet or electromagnet is located in each of the receptacle 508 and the adapter 506.

Figure 6:
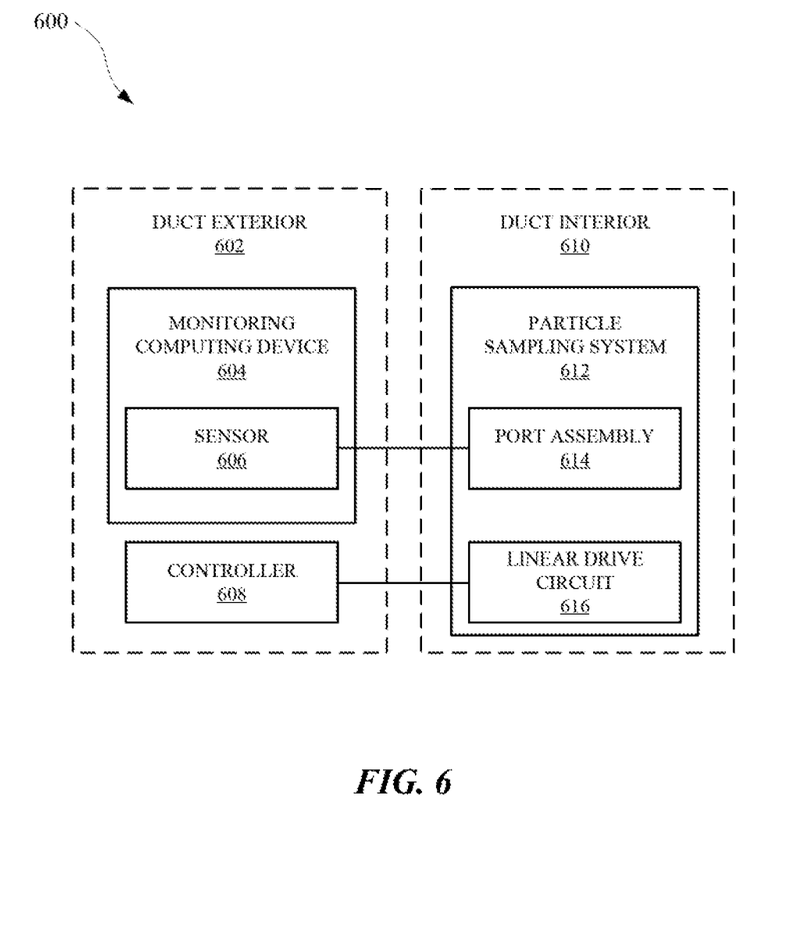
FIG. 6 illustrates a system diagram of a particle sampling system connected to a monitoring computing device and a controller.

FIG. 6 illustrates a system diagram 600 of a particle sampling system 612 connected to a monitoring computing device 604 and a controller 608. The particle sampling system 612 can be located in a duct interior 610 for sampling particles that are passing through a filter in the duct. The monitoring computing device 604 and controller 608 can be located at a duct exterior 602, to eliminate the number of operational parts within the duct interior 610. The monitoring computing device 604 can include one or more sensors 606 for providing data to the monitoring computing device 604 related to particles collected by the particle sampling system 612. The particle sampling system 612 collects samples using a port assembly 614 that can move over a surface of a filter in the duct interior 610 and collect particles that are emitted by the filter. The collected particles can be transferred out of the duct interior 610 via a gas outlet located at a surface of the duct. Otherwise, the duct can be sealed such that particles cannot enter or exit the duct, unless through an inlet or outlet deliberately designed for the duct. The collected particles can reach the sensor 606 of the monitoring computing device 604 and the monitoring computing device 604 can analyze data from the sensor 606 to determine a quality of the filter. As the sensor is receiving the collected particles, the controller 608 can be in communications with a linear drive circuit 616, which can control an electromechanical device that maneuvers the port assembly 614. The electromechanical device can be a magnetic rail drive, a linear servo motor, a linear actuator, and/or any other electromechanical device that can maneuver a port along a path. In some embodiments, the controller 608 can provide power and control signals to the linear drive circuit 616. In other embodiments, the monitoring computing device 604 can provide the power and/or control signals to the linear drive circuit 616. In yet other embodiments, the monitoring computing device 604 can be in communications with the controller 608 for providing feedback to the controller 608 during testing of a filter in the duct.

Figure 7:
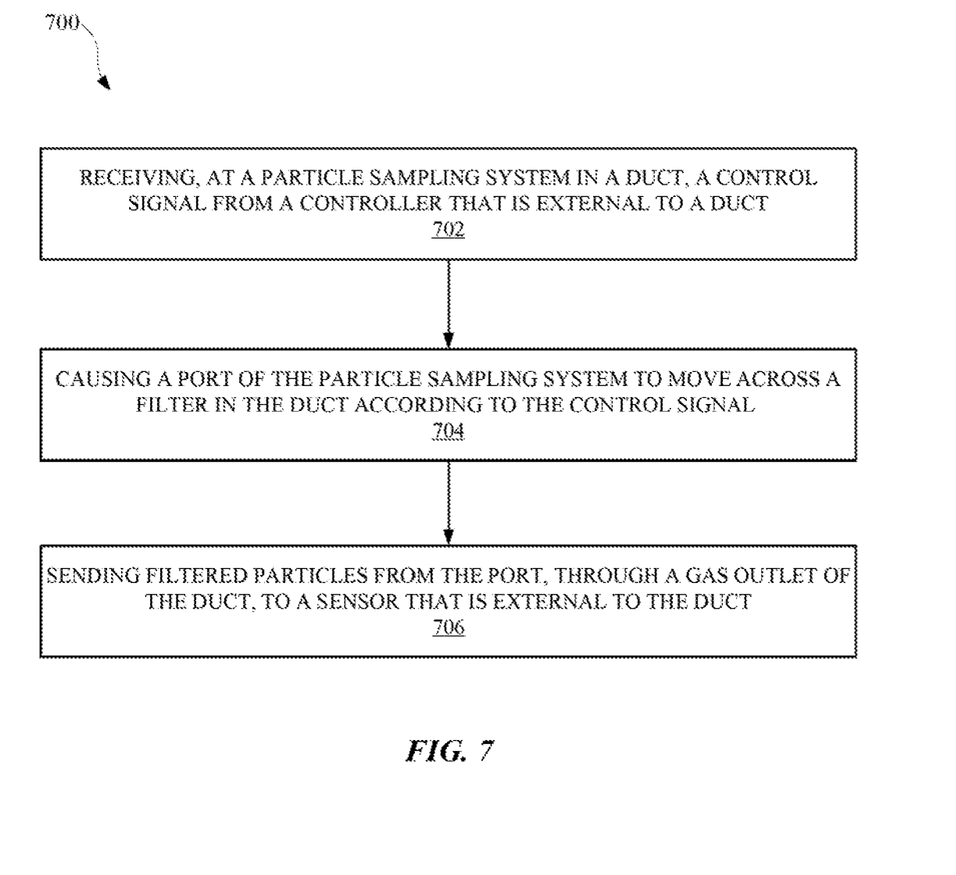
FIG. 7 illustrates a method for performing a filter test using a particle sampling system located inside of a duct that includes the filter.

FIG. 7 illustrates a method 700 for performing a filter test using a particle sampling system located inside of a duct that includes the filter. The method 700 can be performed by the particle sampling system, a controller, and/or any other device capable of controlling a testing operation. The method 700 can include a block 702 of receiving, at a particle sampling system in a duct, a control signal from a controller that is external to the duct. The control signal can be provided over one or more channels from a controller that is external to the duct. Additionally, the control signal can be received by one or more inductors that can create an electromagnetic field that can induce mechanical motion at the particle sampling system. At block 704, one or more ports of the particle sampling system can be caused to move across a filter in the duct according to the control signal and mechanical motion. The motion of the ports can be the result of an interaction between one or more magnets and/or one or more electromagnets, which can maneuver parallel to a width of the filter. At block 706, filtered particles are sent from the port, through a gas outlet of the duct, to a sensor that is external to the duct. The filtered particles can be sent to the sensor for testing, simultaneous to the ports moving across the filter. In this way, the testing of the particles can be automatically controlled without a human interacting with moving parts internal to the duct. This allows for more filters to be tested consistently in a shorter period of time.

Figure 8:
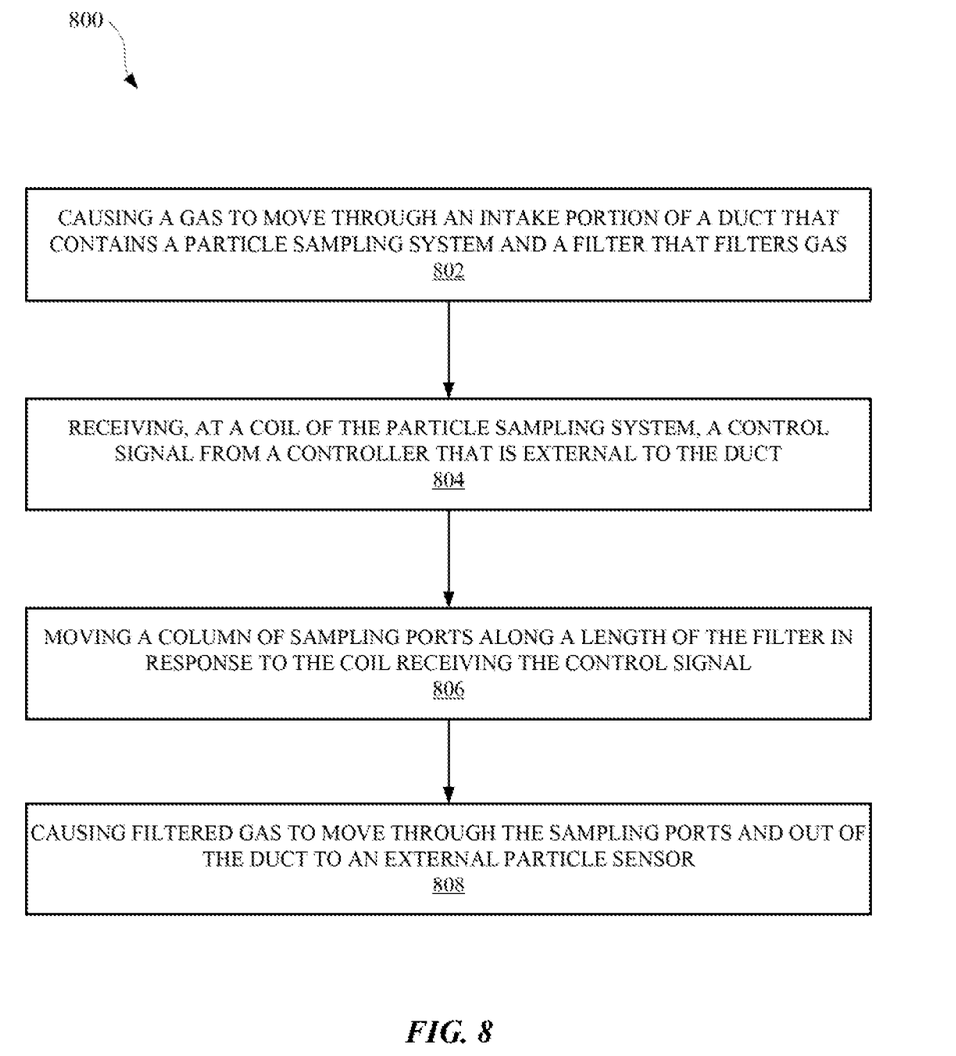
FIG. 8 illustrates a method for testing a filter of a duct using an automatic particle sampling system.

FIG. 8 illustrates a method 800 for testing a filter of a duct using an automatic particle sampling system. The method 800 can be performed by the particle sampling system, a controller, and/or any other device capable of controlling a testing operation. The method 800 can include a block 802 of causing a gas to move through an intake portion of a duct that contains a particle sampling system and a filter that filters the gas. The particle sampling system can include a column of sampling ports and a linear drive system that can maneuver the sampling ports across a surface of the filter for detecting particles that have entered the surface of the filter. At block 804, a control signal from a controller that is external to the duct can be received at a coil of the particle sampling system. The coil can be part of the linear drive system, and the control signal can cause the coil to provide an electromagnetic field. The electromagnetic field can repel and/or attract a magnet or electromagnet of the linear drive system to provide mechanical motion. In some embodiments, the control signal can be received by multiple different coils that act to provide the mechanical motion. The coils can wrap around a rail of the linear drive system, and/or extend over a surface of the linear drive system for effectuating the mechanical motion. At block 806, the mechanical motion from the coil can be used to move a column of sampling ports along a length of the filter. The column of sampling ports can move from one end of the filter to an opposite end of the filter according to instructions encoded in the control signal. Furthermore, the column of sampling ports can oscillate between distal ends of filter during the testing process in order that a continuous stream of particle samples can be collected from different locations on the filter. At block 808, filtered gas can be caused to move through the sampling ports and out of the duct to an external sensor that can provide data related to the properties of the filtered gas and the quality of the filter.

Figure 9:
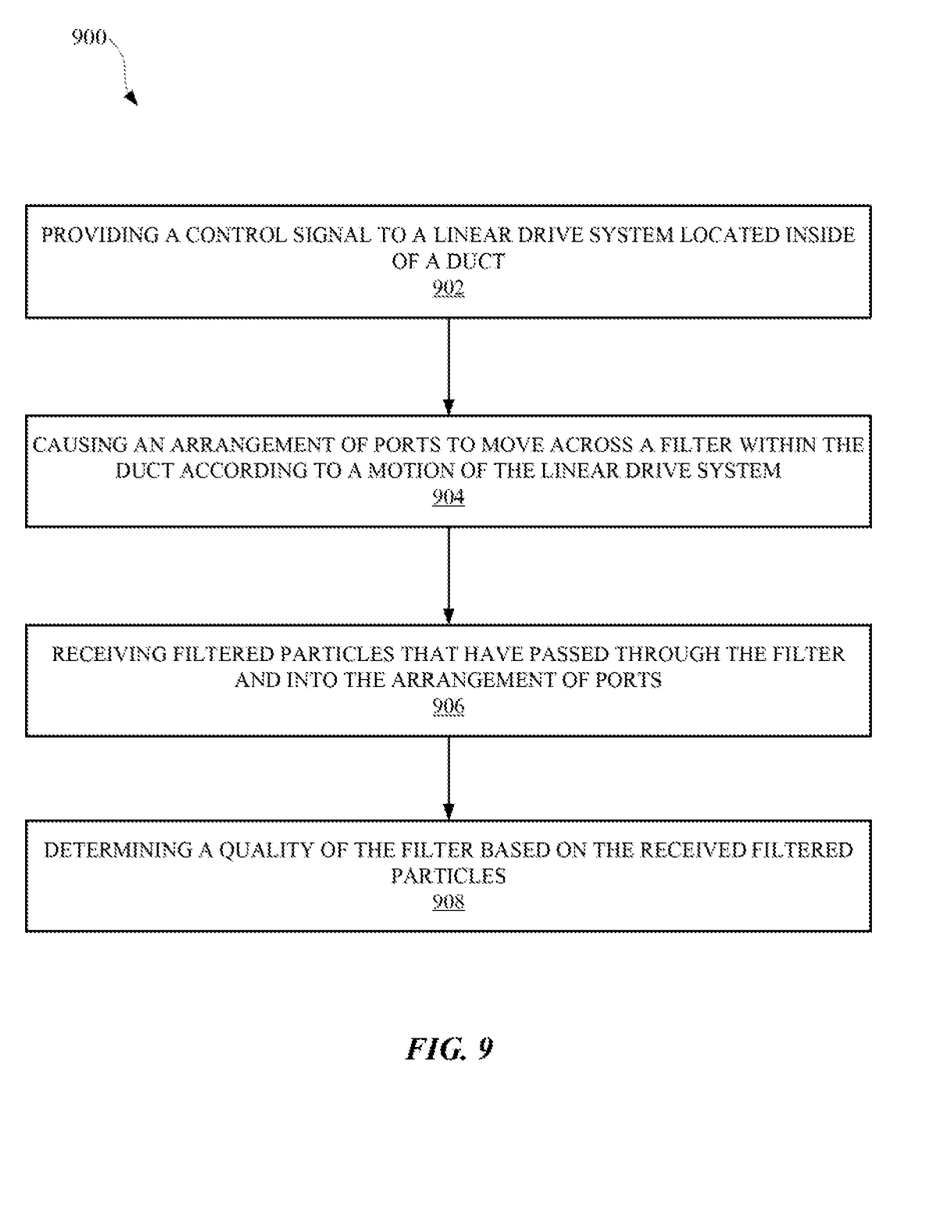
FIG. 9 illustrates a method for controlling a particle sampling system from an exterior of a duct such that all mechanical motion is contained in the interior of the duct and no mechanical motion is transferred through the wall of the duct.

FIG. 9 illustrates a method 900 for controlling a particle sampling system from an exterior of a duct. The method 900 can be performed by a controller, computing device, and/or any other apparatus suitable for controlling a testing operation. The method 900 can include a block 902 of providing a control signal to a linear drive system located inside of the duct. The linear drive system can be a linear servo motor that operates according to control signals of different phases. At block 904, an arrangement of ports can be caused to move across a surface of a filter within the duct according to a motion of the linear drive system. The linear drive system can be attached to the arrangement of ports with a bracket that can extend from an edge of the arrangement of ports, over a surface of a housing of the linear drive system, and into an opening in the linear drive system. The housing can surround the moving parts of the linear drive system in order to prevent any material or debris from entering the linear drive system. At block 906, filtered particles that have passed through the filter and into the arrangement of ports can be received for analysis. At block 908, a quality of the filter can be determined based on the received filtered particles. The quality of the filter can be determined based on the properties of the filtered particles, such as the type of particles, the volume of particles, and/or any other feature indicative of the functionality of a filter.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be understood that certain expressions and reference signs used in the claims pursuant to Rule 6.2(b) of the Patent Cooperation Treaty ("PCT") do not limit the scope.

What is claimed is:

1. A system, comprising:
a duct that includes an air input portion and an air output portion;
a filter receptacle disposed within the duct and configured to receive a filter between the air input portion and the air output portion; and
a particle sampling system configured to collect samples of particles moving through the filter, the particle sampling system comprising a cylindrical coil that is connected to a stacked arrangement of ports and a cylindrical magnetic rail, the cylindrical coil surrounds the cylindrical magnetic rail and is configured to traverse the cylindrical magnetic rail and navigate the stacked arrangement of ports across the filter as particles are moving through the filter, and a housing positioned within the duct that envelops at least a portion of the cylindrical magnetic rail allowing the cylindrical coil, interior to the housing, to traverse a length of the cylindrical magnetic rail while positioning the stacked arrangement of ports exterior to the housing.

2. The system of claim 1, further comprising:
a sensor that is external to the duct and configured to receive the particles collected simultaneously from openings in the stacked arrangement of ports.

3. The system of claim 1, wherein the duct further comprises an outlet valve, and the system further comprises:
a branch valve connected to openings in the stacked arrangement of ports, wherein the branch valve is configured to direct the particles from the openings to the outlet valve.

4. The system of claim 1, further comprising:
a support plate connected to the stacked arrangement of ports and the cylindrical coil, the support plate configured to maintain the stacked arrangement of ports in a direction that is perpendicular to the cylindrical magnetic rail.

5. The system of claim 4, wherein the support plate extends away from the cylindrical magnetic rail through a longitudinal slot within the housing to the stacked arrangement of ports such that the stacked arrangement of ports are maneuverable over a portion of the duct between the filter receptacle and the cylindrical magnetic rail.

6. The system of claim 1, further comprising:
a controller that is connected to the cylindrical coil, the controller configured to cause the stacked arrangement of ports to oscillate between distal ends of the cylindrical magnetic rail.

7. The system of claim 6, wherein the duct includes an electrode located at an outer surface of the duct, the electrode configured to electrically connect the cylindrical coil to the controller.

8. The system of claim 1, wherein the cylindrical coil is separated from the cylindrical magnetic rail by a radial gap circumferentially extending around the cylindrical magnetic rail, wherein the radial gap extends parallel to a width of the filter receptacle.

9. A method for operating a particle sampling system that includes a cylindrical coil for maneuvering a column of sampling ports along a cylindrical magnetic rail, the method comprising:

providing the cylindrical magnetic rail surrounded by the cylindrical coil within a housing positioned internal to a duct, wherein the cylindrical coil is separated from the cylindrical magnetic rail by a radial gap circumferentially extending around the cylindrical magnetic rail;

causing gas to move through an intake portion of the duct that contains the particle sampling system and a filter that filters the gas;

receiving, at the cylindrical coil, a control signal from a controller that is external to the duct, wherein the controller causes the cylindrical coil to traverse the cylindrical magnetic rail;

moving the column of sampling ports external to the housing along a length of the filter within the duct, wherein the column of sampling ports is attached to the cylindrical coil and moves in response to the cylindrical coil receiving the control signal;

maintaining the radial gap circumferentially extending about the cylindrical magnetic rail when moving the cylindrical coil and the column of sampling ports along the cylindrical magnetic rail; and causing filtered gas to move through sampling ports of the column of sampling ports and out of the duct to an external particle sensor.

10. The method of claim 9, wherein the column of sampling ports is configured to traverse the length of the filter in response to receiving the control signal.

11. The method of claim 9, wherein the cylindrical magnetic rail is adjacent to an edge of the filter and the column of sampling ports extends perpendicular to the edge and the cylindrical magnetic rail.

12. The method of claim 9, wherein the control signal is a multiphase signal that causes the cylindrical coil to move horizontally relative to an inner surface of the duct on which the cylindrical magnetic rail is mounted.

13. The method of claim 9, wherein the duct includes an output port from which the filtered gas moves to reach the external particle sensor.

14. A particle sampling system, comprising:

an air duct that includes an air input portion and an air output portion;

an array of ports configured to receive filtered particles passing through a filter that is mounted within the air duct;

a linear drive that includes a magnetic rail and a cylindrical coil, wherein the magnetic rail is a shaft and the cylindrical coil surrounds the shaft, and wherein the cylindrical coil is separated from the shaft by a radial gap circumferentially extending around the shaft;

the linear drive connected to the array of ports and configured to maneuver the array of ports over a surface of the filter;

a support plate connected to the array of ports and the cylindrical coil of the linear drive, the support plate configured to transfer mechanical energy from the cylindrical coil to the array of ports and maintain a position of the array of ports between the filter and the linear drive; and a housing positioned within the air duct, wherein the housing includes an opening facing downstream in a direction from the air input portion towards the air output portion, and wherein the housing at least partially envelopes the linear drive and the support plate extends through the opening and linearly travels along the opening of the housing while positioning the array of ports exterior to the housing.

15. The particle sampling system of claim 14, wherein the cylindrical coil includes adjacent coils whose polarity changes in order to maneuver the array of ports over the surface of the filter.

16. The particle sampling system of claim 14, wherein the linear drive includes a series of abutting magnets extending in a perpendicular direction relative to the array of ports.

17. The particle sampling system of claim 14, wherein the array of ports are arranged in a single column that is configured to move to, and between, distal ends of the filter according to a motion of the cylindrical coil.

18. The particle sampling system of claim 14, further comprising:
 a branch valve that is connected to the array of ports and consolidates streams of gases received by the array of ports.

19. The particle sampling system claim 18, further comprising:
 a particle sensor that is connected to the branch valve and is configured to receive a consolidated stream of gas from the branch valve.

20. The particle sampling system claim 18 wherein the opening of the housing is a longitudinal slot extending perpendicular to the air flow in the direction from the air input portion towards the air output portion.

21. The particle sampling system claim 18 further including one or more guides positioned within the housing and extending parallel to the linear drive.

\* \* \* \* \*

UNITED STATES PATENT AND TRADEMARK OFFICE
CERTIFICATE OF CORRECTION

PATENT NO. : 10,578,521 B1
APPLICATION NO. : 15/591881
DATED : March 3, 2020
INVENTOR(S) : Satish Dinakaran and Kenneth Beacham It is certified that error appears in the above-identified patent and that said Letters Patent is hereby corrected as shown below:

On the Title Page

Page 2, item (56), Column 1, under 'References cited', Line 14, delete "Bamabo et. al." and insert -- Barnabo et. al. --, therefor.

In the Specification

In Column 1, Line 34, delete "fitter" and insert -- filter --, therefor.

In Column 6, Line 13, delete "100" and insert -- 110 --, therefor.

In Column 7, Line 18, delete "fitter" and insert -- filter --, therefor.

In the Claims

In Column 15, Claim 19, Line 17, delete "system" and insert -- system of --, therefor.

In Column 15, Claim 20, Line 22, delete "system" and insert -- system of --, therefor.

In Column 15, Claim 20, Line 22, delete "18" and insert -- 14 --, therefor.

In Column 15, Claim 21, Line 26, delete "system" and insert -- system of --, therefor.

In Column 15, Claim 21, Line 26, delete "18" and insert -- 14 --, therefor.

Signed and Sealed this
Sixth Day of October, 2020

Andrei Iancu
*Director of the United States Patent and Trademark Office*